United States Patent
Phillips

(10) Patent No.: US 9,278,235 B1
(45) Date of Patent: Mar. 8, 2016

(54) ADAPTIVE DEMAND OXYGEN DELIVERY SYSTEM

(75) Inventors: Robert E. Phillips, Fallbrook, CA (US); Lynn H. Phillips, legal representative, Fallbrook, CA (US)

(73) Assignee: Lynn H. Phillips, Fallbrook, CA (US), Trustee ( * ) Notice: Subject to any disclaimer, the term of this patent is extended or adjusted under 35 U.S.C. 154(b) by 1021 days.

(21) Appl. No.: 13/385,862

(22) Filed: Mar. 12, 2012

(51) Int. Cl.
*A61M 16/20* (2006.01)
*A62B 7/04* (2006.01)
*A62B 9/02* (2006.01)
*A61M 16/06* (2006.01)

(52) U.S. Cl.
CPC .............. *A62B 7/04* (2013.01); *A61M 16/0677* (2014.02); *A61M 16/20* (2013.01); *A62B 9/022* (2013.01); *A61M 16/0666* (2013.01)

(58) Field of Classification Search
CPC ...................... A61M 16/0666; A61M 16/0672; A61M 16/0677; A61M 16/20; A62B 7/04
USPC ............ 128/205.16, 205.24, 207.12, 207.14, 128/207.16, 207.18; 137/907, 908, 616.7, 137/505.38, 505.39; 251/340, 304, 310
See application file for complete search history.

(56) References Cited

U.S. PATENT DOCUMENTS

| | | | | |
|---|---|---|---|---|
| 4,172,467 A * | 10/1979 | Warnow | .................. | 137/494 |
| 4,572,176 A * | 2/1986 | Walther | .................. | 128/204.26 |
| 4,572,177 A * | 2/1986 | Tiep et al. | .................. | 128/205.17 |
| 5,343,858 A * | 9/1994 | Winefordner et al. | ... | 128/204.26 |
| 5,928,189 A * | 7/1999 | Phillips et al. | .................. | 604/65 |
| 7,328,703 B1 * | 2/2008 | Tiep | .................. | 128/207.18 |
| 8,327,848 B2 * | 12/2012 | Ho et al. | .................. | 128/205.24 |

* cited by examiner

*Primary Examiner* — Justine Yu
*Assistant Examiner* — Douglas Sul

(57) ABSTRACT

The delivery system has a control body in the form of a pendant to which oxygen is delivered and from which the oxygen is delivered to the patient. The body includes a reservoir which has a constant oxygen supply orifice. During rest conditions, the patient breathes only a portion of the reservoir contents. During physical activity, the patient breathes more deeply and inhales more oxygen from the reservoir. The reservoir has a flexible diaphragm and when breathing more deeply, the diaphragm moves to open a bolus oxygen supply valve to introduce a bolus of additional oxygen to the reservoir and thus to the patient.

3 Claims, 8 Drawing Sheets

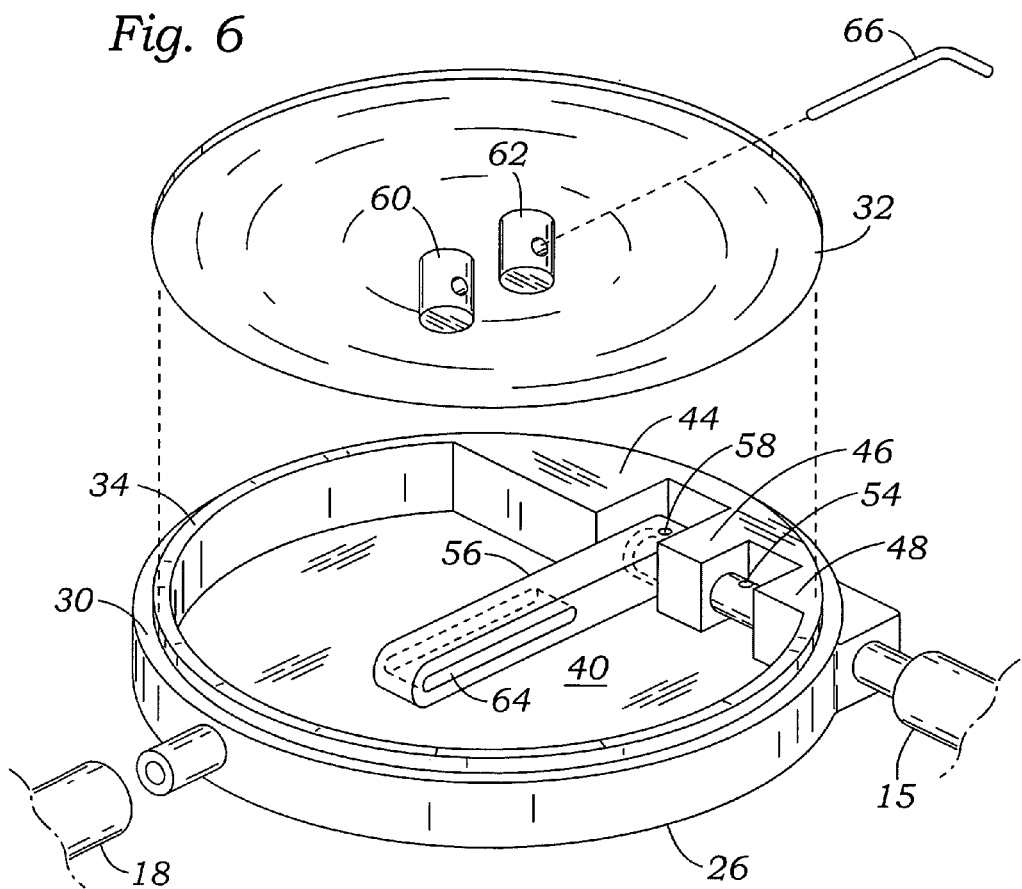
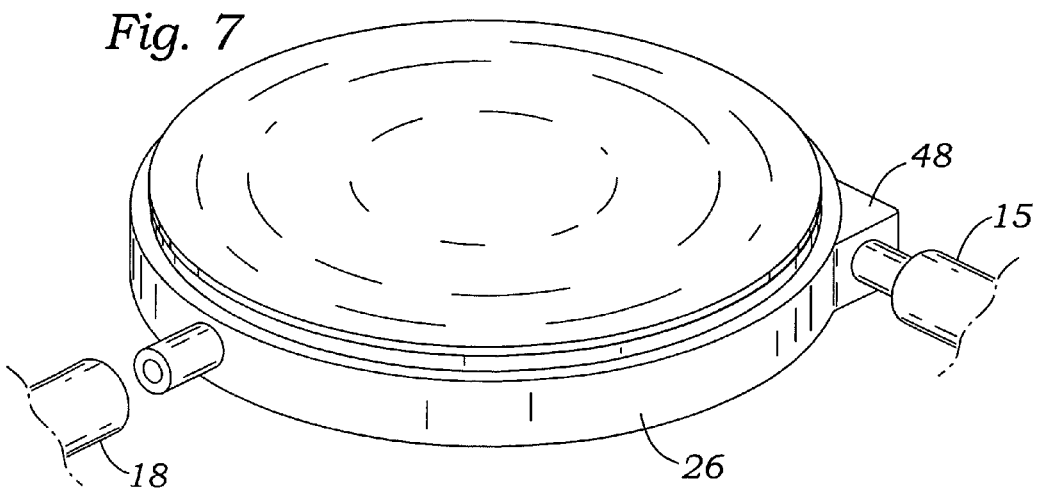

ADAPTIVE DEMAND OXYGEN DELIVERY SYSTEM

BACKGROUND

For hypoxemic patients with chronic obstructive pulmonary disorder (COPD) and other restrictive lung diseases, continuous flow of supplemental oxygen has proven to improve survival and quality of life. Large patient care facilities often have large oxygen supplies, so conservation may not be a critical factor. Patients in hospitals are often prescribed 2 liters per minute, which is more than many patients require, especially when they are sedentary. In home settings, some patients are supplied with oxygen by means of an oxygen concentrator. Such devices are conventionally set at delivery rates which are sufficient for sedentary and moderately active patient requirements. The oxygen concentrators deliver oxygen at 6 PSI.

A major development in oxygen therapy was the introduction of oxygen conserving devices. Such include reservoir cannulas, pulse demand oxygen delivery devices, and transtracheal oxygen systems. Mobile patients, who carry pressurized oxygen tanks with them as they move around, are helped by oxygen conservation. These patients carry tanks with them, and the tanks are necessarily small. Conservation provides greater mobility. They can go greater distances for longer times, if the oxygen is conserved.

The essence of portable therapy is to permit the patient to be supplied with oxygen whether sedentary or active. There is a need for automatically adjusting the oxygen delivery to adapt to the patient's changing oxygen requirements. Systems which adjust to patient activity are more recent. One adaptive delivery device which is presently available is an electronic demand system with a motion sensor. The device is selectively set for sedentary or active. When the patient begins to exert, the device senses the motion and boosts delivery to the active setting. This device is only operative for pulse demand oxygen delivery. Many patients do not oxygenate well on pulse delivery systems and therefore require continuous oxygen flow. Examples of these patients include those with interstitial lung disease, severe COPD, and advanced lung cancer.

It is desirable to provide a continuous flow oxygen delivery device which regulates the amount of oxygen delivered to the patient in accordance with their physical activity.

BRIEF SUMMARY OF THE INVENTION

In order to aid in the understanding of this invention it can be stated in essentially summary form that it is directed to an adaptive oxygen delivery system. The system includes a control body which contains a reservoir into which oxygen is delivered through first and second passages. The first passage supplies continuous oxygen flow, as required by the sedentary patient. The second passage provides a bolus of additional flow and is opened when the patient takes a deeper breath. The breath volume acts on a variable size reservoir which opens the second passage when the reservoir oxygen volume is decreased by increased inhalation volume.

It is a purpose and advantage of this invention to provide an adaptive continuous flow oxygen supply system which supplies more oxygen to the patient when he is active as compared to being sedentary.

It is another purpose and advantage of this invention to provide an adaptive demand oxygen delivery system which includes a reservoir which is supplied by first and second passages, the first passage providing a sufficient continuous flow of oxygen for a sedentary patient and a second passage which is opened upon a patient's more deep breathing to supply a bolus of addition oxygen when he is active.

Another purpose and advantage of this invention is to provide an oxygen delivery system which is responsive to patient's activity and is suitable for use with an oxygen concentrator.

It is another purpose and advantage of this invention to provide an adaptive oxygen delivery system It is a further purpose and advantage of this invention to provide an adaptive oxygen delivery system which operates with continuous flow and thus can be utilized with continuous flow portable oxygen therapy.

Other purposes and advantages of this invention will be further understood by reference to the following description, the claims, and the attached drawings.

BRIEF DESCRIPTION OF THE DRAWINGS

FIG. 6 is an exploded view showing the reservoir diaphragm in projected position above the control body base.

FIG. 7 shows the diaphragm in place on the base.

DESCRIPTION OF THE PREFERRED EMBODIMENT

Figure 1:
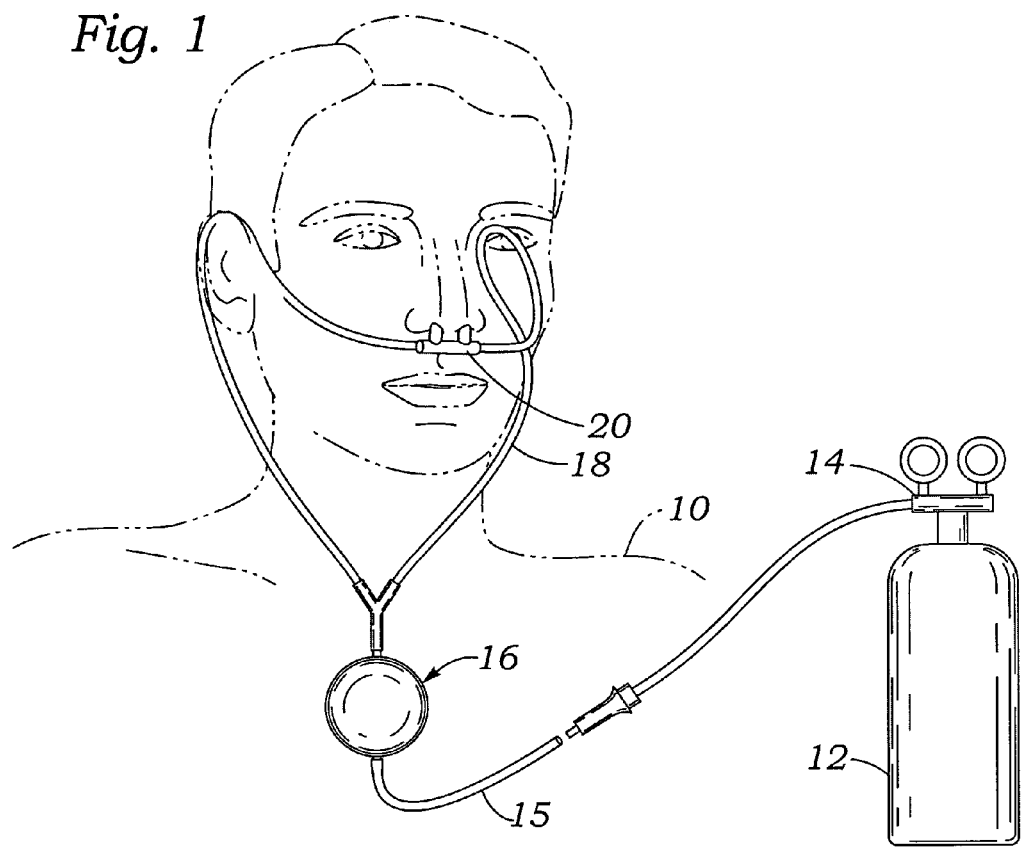
FIG. 1 is view of the adaptive demand oxygen delivery system, as utilized by a patient.

FIG. 1 shows a patient 10 with prescribed therapeutic oxygen. The oxygen is delivered in a convenient way such as from a pressurized tank 12 or an oxygen concentrator. The oxygen from the tank 12 is regulated and pressurized by pressure regulator 14 where the oxygen under pressure is delivered to control body 16. The source of oxygen may be an oxygen concentrator which has its own internal pressure regulator or any other convenient source. The control body which is shown in the form of pendant 16, which is described in detail below. Control body 16 is useful and operative at pressures delivered from a pressurized oxygen cylinder or from an oxygen concentrator. The control body is convenient in the form of a pendant, as illustrated.

Figure 2:
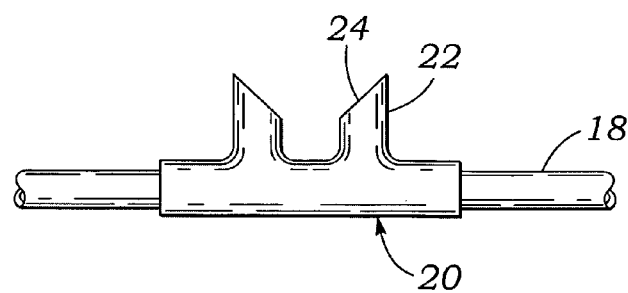
FIG. 2 is an enlarged view of the nasal cannula.

The control body delivers the oxygen to the nasal passages through tubes 18 to deliver the oxygen to the nasal cannula 20. As seen in FIG. 2, the nasal cannula 20 comprises a delivery tube 22 into each nostril. The delivery tube has an angular face 24 to increase the delivery area.

Figure 3:
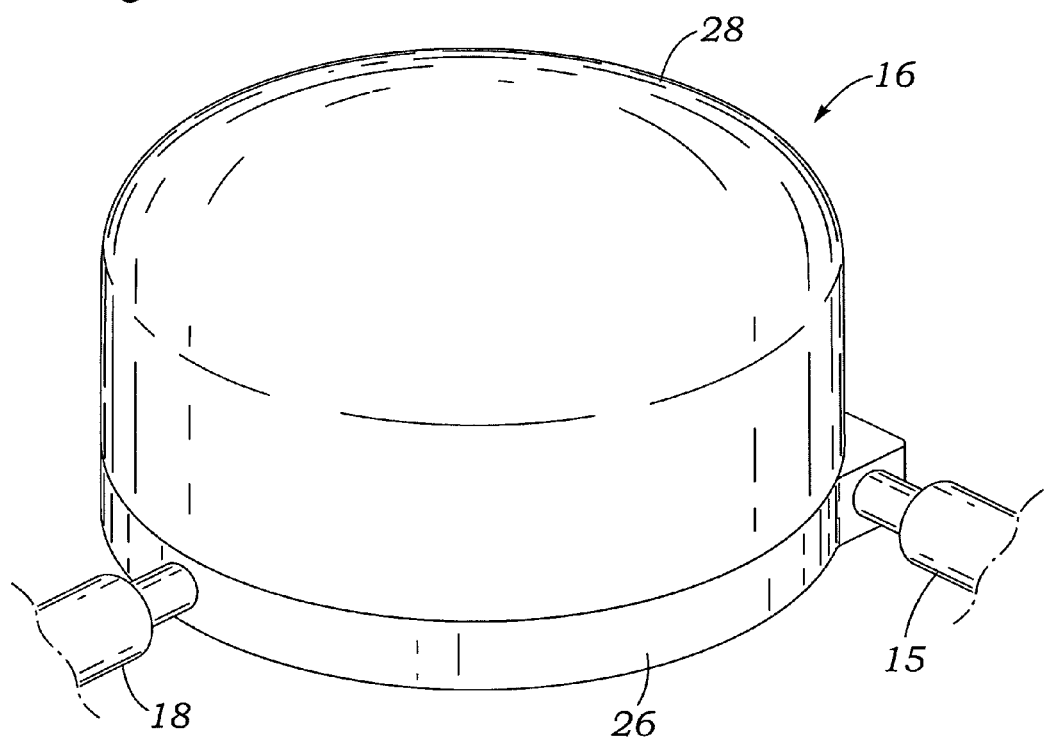
FIG. 3 is a perspective view of the control body of the oxygen delivery system.
Figure 4:
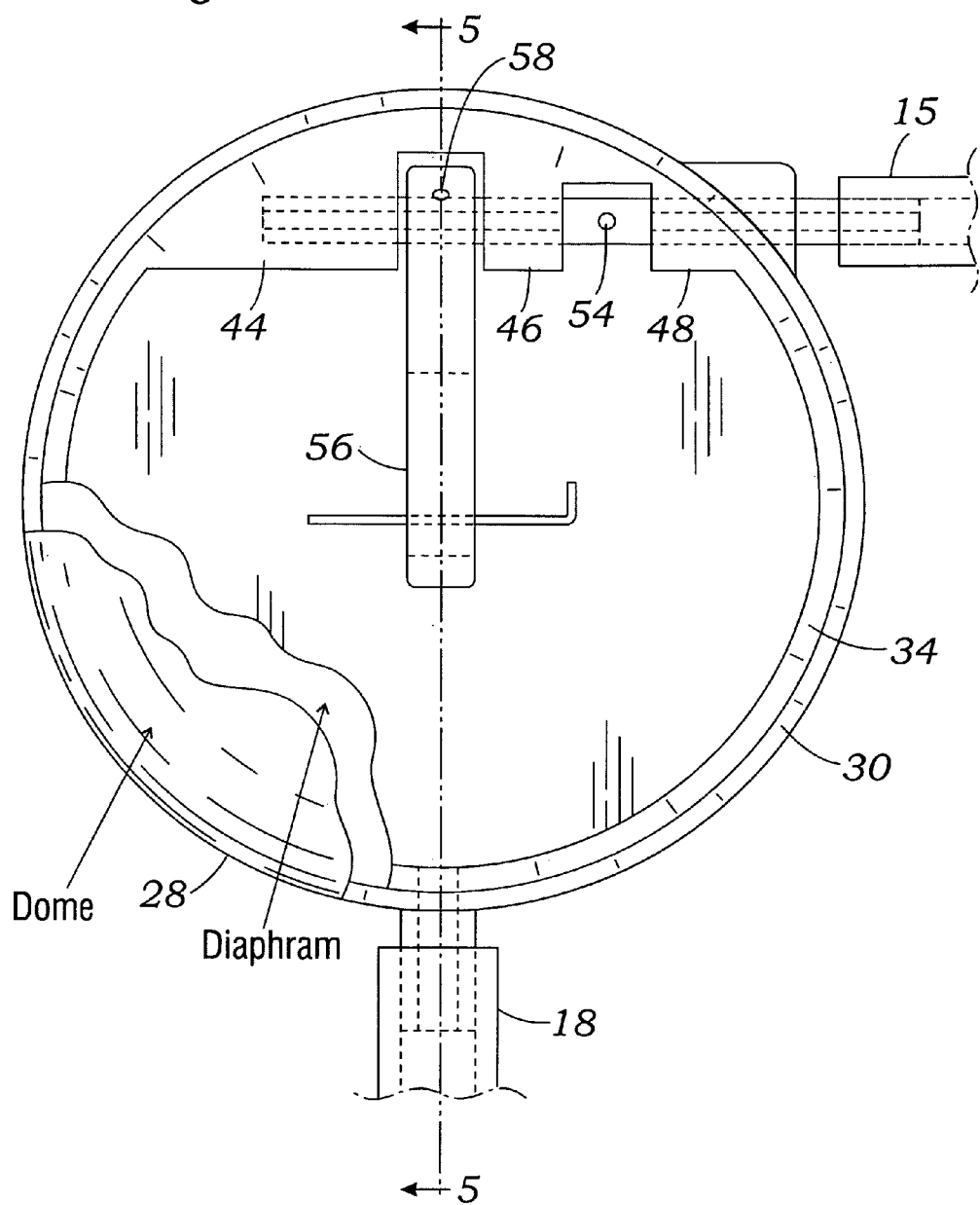
FIG. 4 is a plan view of the control body in the form of a control body, with parts of the dome and diaphragm broken away.
Figure 5:
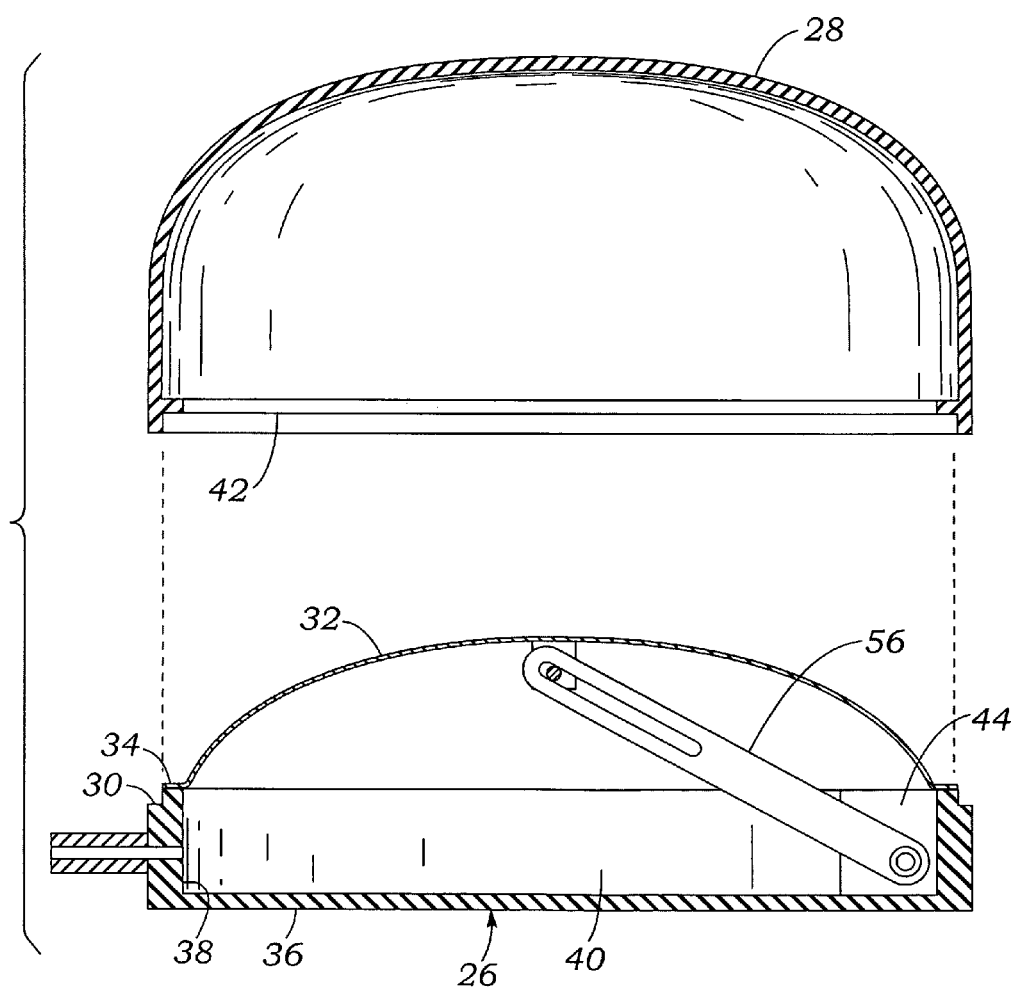
FIG. 5 is a sectional view through the center of the control body with the cover dome in projected position, as seen generally along line 5-5 of FIG. 4.

Control body 16 is shown in perspective view in FIG. 3. The inlet tube 15 and outlet tube 18 are connected to base 26. Dome 28 is mounted on the base. The dome is ventilated to prevent interior pressure build up. FIG. 5 shows dome 28 projected above base 26. The dome fits onto a shoulder 30. The top of the base carries flexible and elastic diaphragm 32, which rests on the top rim 34 of the base 26. The base 26 is comprised of floor 36 which has an upstanding wall 38 which terminates in shoulder 30 and top rim 34. This defines reservoir space 30 above the floor, below the diaphragm, and between the walls. The reservoir space is variable in volume because the diaphragm 32 is flexible and elastic. The dome 28 has an interior flange 42 which engages down on the top edges of diaphragm 32 where the diaphragm is attached to the top rim 34. Thus, the dome clamps the diaphragm in place around its edges. As seen in FIGS. 3 and 4, the outlet tube 18 is connected to the reservoir space 40. Thus the oxygen is delivered from the reservoir space out through tube 18.

Figure 8:
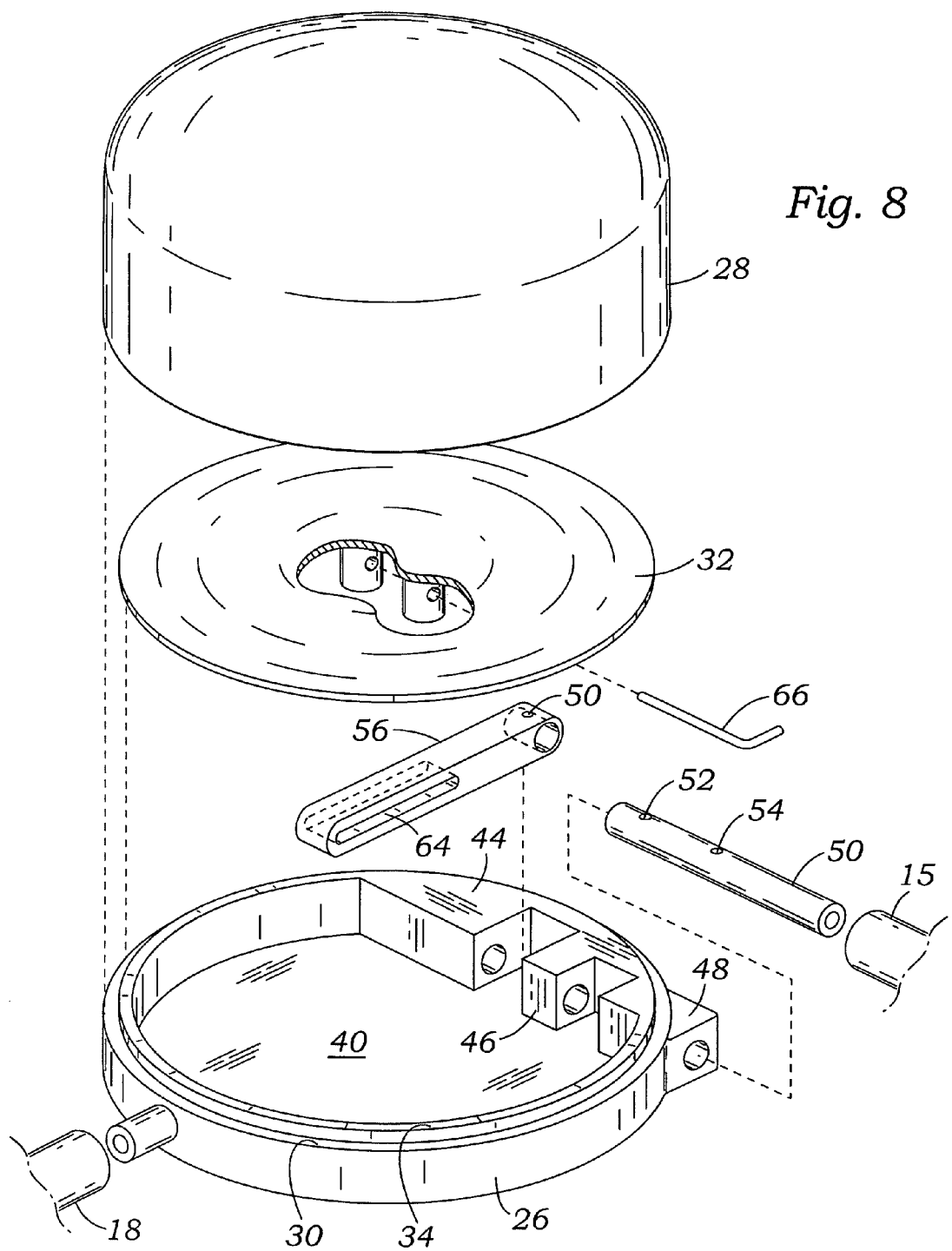
FIG. 8 shows an exploded view of the control body, with parts broken away and parts taken in section.

Oxygen flow into the space 40 is controlled by two orifices. As is seen in FIGS. 4, 6, and 8, base 26 contains bosses 44, 46, and 48 therein. The bosses are bored to receive control tube 50. As seen in FIG. 8, the control tube 50 receives oxygen from the supply tube 15. Control tube 50 is pressed into the bosses. The control tube 50 has two orifices therein. Orifices 52 and 54 are seen in FIG. 8. Orifice 54 is seen in FIGS. 4, 6, and 8. As is seen in these FIGURES, the orifice 54 is positioned between the bosses 46 and 48, and thus is not obstructed. It is sized to continuously deliver to the reservoir space oxygen at a rate as prescribed for sedentary state of the patient. One half liter per minute is a usual dose.

Figure 13:
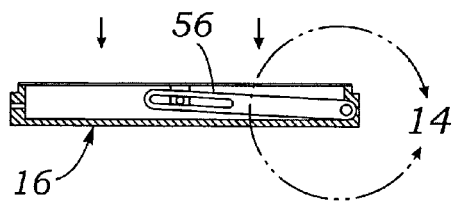
FIG. 13 is similar to FIG. 9, but showing the reservoir diaphragm in the uninflated position.
Figure 14:
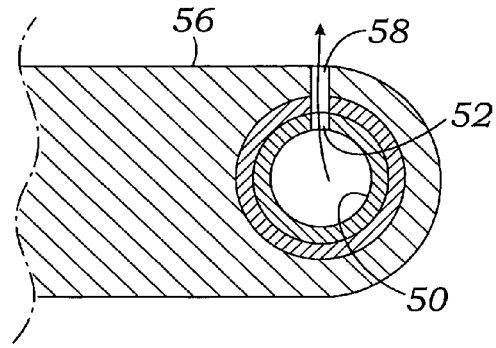
FIG. 14 is an enlarged view of the valve detail as seen along line 14 of FIG. 13.
Figure 15:
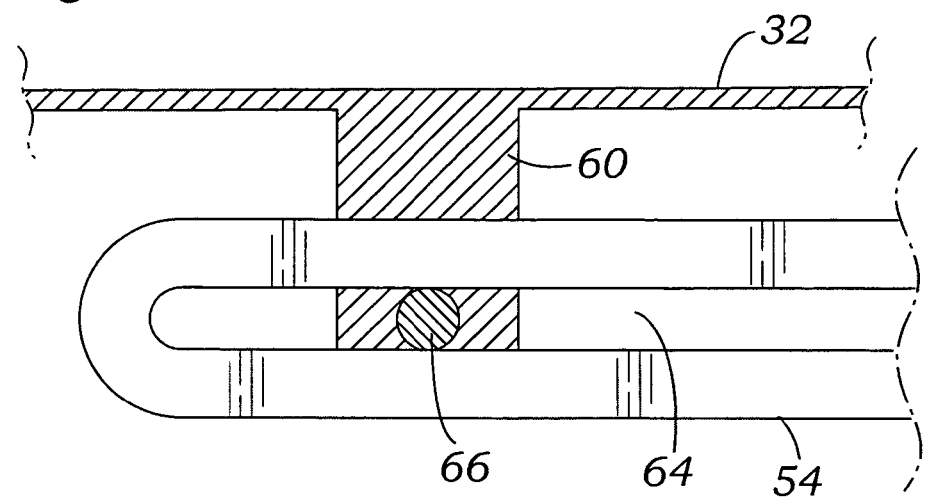
FIG. 15 is an enlarged detail showing the connection of the valve arm to the reservoir diaphragm.
Figure 16:
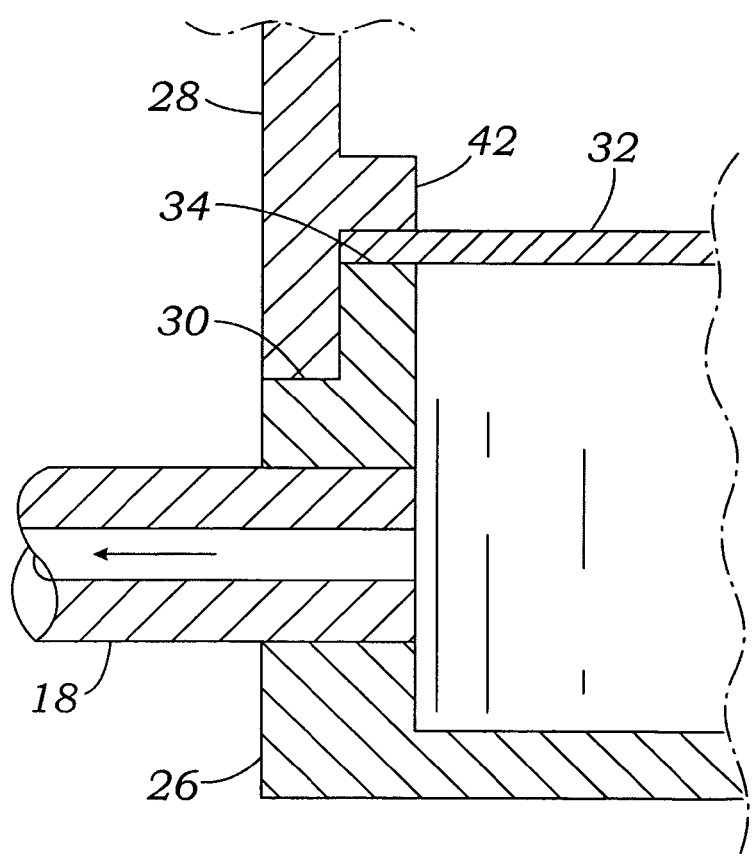
FIG. 16 is an enlarged sectional detail with parts broken away showing the placement of the reservoir diaphragm and the dome on the control body base.

Valve arm 56 is pivotally mounted on control tube 50 between the bosses 44 and 46. The valve arm covers orifice 52. Port 58 in arm 56 aligns with orifice 52 when the valve arm is in its lowest position, as shown in FIGS. 13 and 14, and does not align when the valve arm is in the raised position as shown in FIGS. 9-12. This function will be further described below.

The valve arm 56 is positioned by diaphragm 32. As seen in FIGS. 5, 6, and 8, the diaphragm 32 has two posts 60 and 62 integrally formed therewith or attached thereto. The posts are spaced sufficiently to receive the valve arm 56 therebetween. The valve arm 56 has a slot 64 therein which can lie between the posts. When between the posts, pin 66 is inserted through openings in the posts and through the slot 64 so that the valve arm goes up and down in accordance with inflation of the diaphragm. In this way, the position of the diaphragm controls the opening of orifice 52. When open, orifice 52 supplies an additional bolus of oxygen at a rate of one liter per minute, for example, to the reservoir 40.

Figure 9:
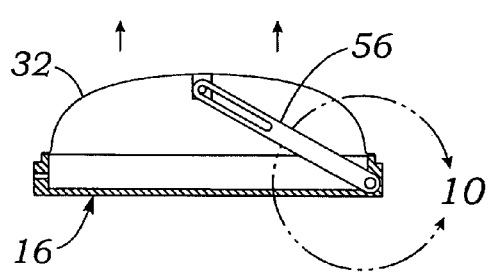
FIG. 9 is a transverse section through the control body, generally along line 5-5 of FIG. 4, showing the reservoir diaphragm in the fully inflated position.
Figure 10:
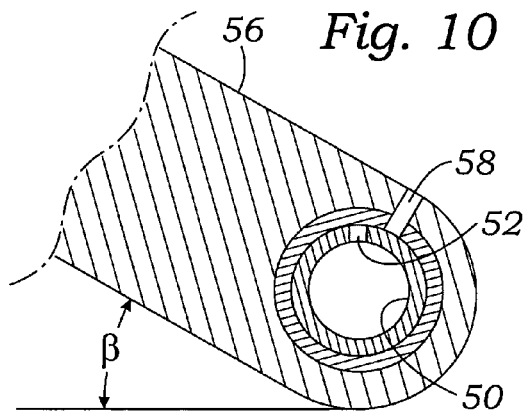
FIG. 10 is an enlarged sectional view with parts broken away showing the valve position at this degree of inflation.
Figure 11:
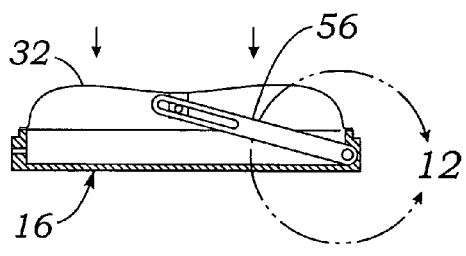
FIG. 11 is similar to FIG. 9, showing the reservoir diaphragm half inflated.
Figure 12:
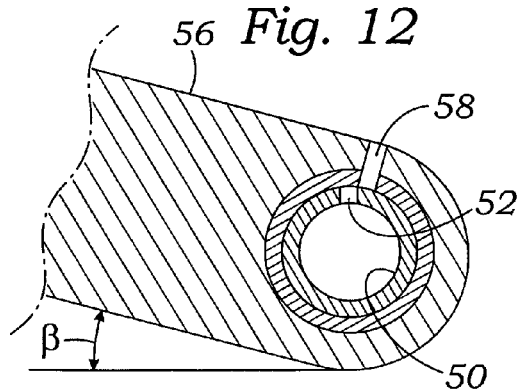
FIG. 12 is an enlarged detail of the valve position in FIG. 11.

FIGS. 9 and 10 illustrate the diaphragm position where the user is at rest and has exhaled. The diaphragm 32 is inflated, the valve arm 56 is in the raised position, and bolus flow orifice 52 is closed, see FIG. 10. Continuous flow through orifice 54 into the reservoir is at 5 milliliters per second. Total volume in the inflated reservoir is 40 milliliters. Assuming the patient is sedentary and at rest, when he inhales, he inhales about half of the reservoir volume so that the reservoir diaphragm moves down about half way, as seen in FIG. 11. In this position of the valve arm, the port 58 is not quite over the bolu8s flow orifice 52. Thus, there is no supplemental oxygen flow.

When the patient is active, he breathes both more deeply and at a higher respiration rate. Thus, the active patient inhales substantially the entire content of the reservoir volume and the valve control arm 56 moves angularly down as illustrated in FIGS. 13 and 14. This moves port 58 into alignment with the high rate bolus flow orifice 52. The high flow orifice delivers a 20 milliliter bolus of oxygen in about 150 milliseconds. This delivery of bolus oxygen raises the control arm 56 to the position shown in FIG. 11 to cut off the bolus flow. Both the patient's exhalation and the continuous flow through the continuous flow orifice 54 aid in inflating the diaphragm 32. As the arm rises to the position of FIG. 11, the bolus flow orifice 52 is cut off. Thus the additional oxygen is delivered through the bolus flow orifice 52 and the flow is cut off when the arm raises to and above the position of FIGS. 9 and 11. The patient receives oxygen in accordance with activity to actively conserve oxygen.

This invention has been described in its presently preferred best mode. It is clear that it is susceptible to numerous modes and embodiments within the scope of the following claims.

The invention claimed is:

1. An adaptive demand oxygen delivering system comprising:
   a control body, structures including an inlet tube on said control body to receive oxygen under pressure from an oxygen supply and to deliver oxygen to the patient;
   a reservoir in said control body connected to said structure to receive oxygen from the supply, said reservoir being connected to said structure to deliver oxygen, said reservoir being of variable volume, said reservoir having a flexible diaphragm to accomplish changes in reservoir volume, said flexible diaphragm having a deflected position wherein said reservoir is substantially fully inflated and a substantially undeflected position where said reservoir has a minimum volume, and an immediate position therebetween, said reservoir being sized so that patient inhalation from said reservoir moves said diaphragm from said substantially fully inflated position to said intermediate position during patient rest conditions and patient inhalation moves said diaphragm from said substantially fully inflated position to said substantially undeflected position while the patient is active;
   a first orifice in said inlet tube between said oxygen receiving structure and said reservoir, said first orifice being sized to deliver sufficient oxygen to the patient while sedentary, and;
   a second orifice in said inlet tube between said oxygen receiving structure and said reservoir, said second orifice having a valve therein, said valve being comprised of a valve arm which is connected to be moved by said flexible diaphragm, said valve arm being configured to position a port over said second orifice when said flexible diaphragm is between its intermediate and substantially undeflected positions, so that said valves opens said second orifice only when said diaphragm is between its substantially undeflected position and its intermediate position.

2. An adaptive demand oxygen delivery system comprising:
   a body;
   a reservoir structure in said body, said reservoir structure having a bottom and having walls, a single flexible diaphragm attached to said walls to define a closed reservoir space within said reservoir structure, said body having inlet and outlet connections to said reservoir so that an oxygen supply is connectable to said inlet connection and delivery structure to a patient is connectable to said outlet connection;

said body having a bore therein, said inlet structure comprising a tube in said bore, said tube having said first and second orifices therein, said first orifice being exposed to said reservoir space, a valve comprising an arm mounted on said tube, said arm having a port therein which is in alignment with said second orifice when said reservoir is between its intermediate and depleted positions and is out of alignment when said reservoir is between its intermediate and inflated positions;

said first orifice being exposed to said reservoir to deliver a constant flow of oxygen to said reservoir, said second orifice being to supply a bolus of oxygen from said inlet connection to said reservoir;

said single diaphragm having a maximum inflation position, a minimum inflation position, and an intermediate inflation position, said valve are being connected to said diaphragm so that said second orifice is open when said diaphragm is between said minimum inflation position and said intermediate inflation position and is closed when said diaphragm is between its intermediate inflation position and its maximum inflation position, said reservoir being sized so that when a patient at rest inhales oxygen from said delivery system said diaphragm moves from its maximum inflation position to its intermediate inflation position so that said second orifice is not opened, and when an active patient inhales from said delivery system, said diaphragm moves from its maximum inflation position past its intermediate inflation position toward said minimum inflation position so that said second orifice opens to supply a bolus of additional oxygen to said reservoir.

3. The adaptive demand oxygen delivery system of claim 2 wherein said valve arm is connected to said diaphragm by means of at least one post on said diaphragm and connection structure between said post and said valve arm.

* * * * *